United States Patent [19]

Magro et al.

[11] Patent Number: 4,738,658
[45] Date of Patent: Apr. 19, 1988

[54] TAPERED HEMOSTATIC DEVICE FOR USE IN CONJUNCTION WITH A CATHETER FOR ALLEVIATING BLOOD LEAKAGE AND METHOD FOR USING SAME

[75] Inventors: Alfred E. Magro, Woburn; Michael Rishton, Reading, both of Mass.

[73] Assignee: Aries Medical Incorporated, Woburn, Mass.

[21] Appl. No.: 909,698

[22] Filed: Sep. 19, 1986

[51] Int. Cl.$^4$ .................... A61M 5/00; A61M 25/00
[52] U.S. Cl. ...................................... 604/53; 604/158; 604/168; 604/280
[58] Field of Search ................................ 604/158–171, 604/53, 280

[56] References Cited

U.S. PATENT DOCUMENTS

| | | | |
|---|---|---|---|
| 3,877,429 | 4/1975 | Rasumoff | 128/214 |
| 3,921,631 | 11/1975 | Thompson | 604/53 |
| 4,149,535 | 4/1979 | Volder | 604/164 X |
| 4,239,042 | 12/1980 | Asai | 128/214 |
| 4,304,231 | 12/1981 | Bodicky et al. | 128/214 |
| 4,326,520 | 4/1982 | Alley | 128/214 |
| 4,327,722 | 5/1982 | Groshong et al. | 128/214 |
| 4,451,256 | 5/1984 | Weikl et al. | 604/164 |
| 4,610,671 | 9/1986 | Luther | 604/168 |
| 4,629,450 | 12/1986 | Suzuki et al. | 604/164 |

FOREIGN PATENT DOCUMENTS

| | | | |
|---|---|---|---|
| 139091 | 5/1985 | European Pat. Off. | 604/168 |

OTHER PUBLICATIONS

Tegtmeyer et al.—Radiology, 139:231–232, Apr., 1981.

*Primary Examiner*—Dalton L. Truluck
*Attorney, Agent, or Firm*—David G. Conlin; George W. Neuner; Ronald I. Eisenstein

[57] ABSTRACT

A method of stopping bleeding around a catheter when an insertion sheath is removed is disclosed. This method involves using a novel tapered hemostatic device that can be moved along the catheter tube into the puncture site. The tapered hemostatic device of the present invention has an inner diameter that is just sufficient to permit the catheter tube to slide therethrough and a tapered outer diameter which at the distal end of the device is slightly larger than the inside diameter and at the proximal end of the device is at least as large as the outside diameter of the insertion sheath used to place the catheter in the blood vessel. The hemostatic device is moved down the catheter tube into the puncture site where the device stops the bleeding. Using a hemostasis cuff at the proximal end of the device to stop blood flow between the tapered hemostatic device of the invention and the catheter is also disclosed.

The hemostatic device may contain a longitudinal channel along the wall of the device. Preferably, this channel is along the inner wall of the device. This channel permits blood to flow therethrough when the distal end of the device enters the blood vessel thereby serving as an indicator if the hemostatic device is in the blood vessel.

19 Claims, 2 Drawing Sheets

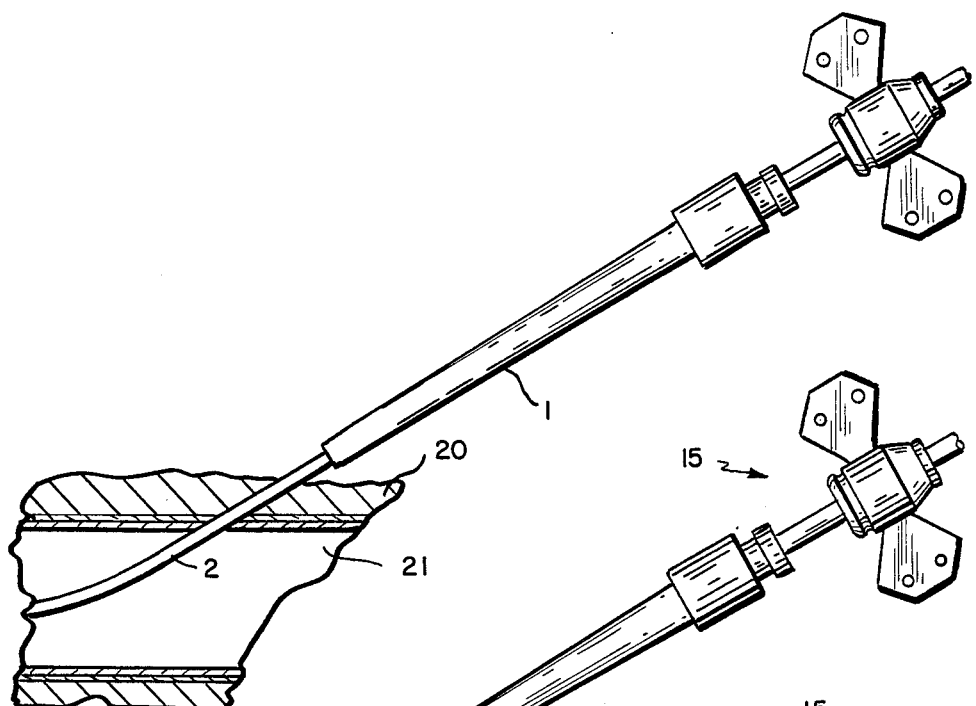
FIG.10A
FIG.10B
FIG.10C
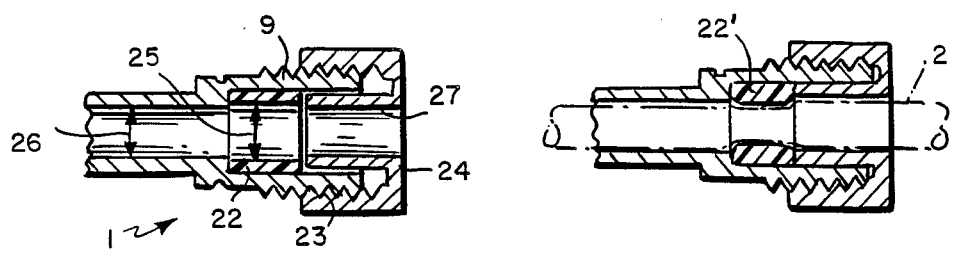
FIG.11A
FIG.11B

TAPERED HEMOSTATIC DEVICE FOR USE IN CONJUNCTION WITH A CATHETER FOR ALLEVIATING BLOOD LEAKAGE AND METHOD FOR USING SAME

The present invention is directed to an improvement in the method of placing catheters into a blood vessel, and particularly to a novel tapered device for alleviating the leakage of blood after the insertion sheath is removed, and a catheter set including on the catheter a tapered device for alleviating blood leakage.

Intra aortic balloon pump (IABP) therapy is the treatment of choice for patients suffering from left ventricular failure. IABP therapy is applied by placing a catheter mounted balloon in the aorta by way of the femoral artery.

Initially, the technique generally involved a surgical cutdown to the femoral artery and the direct placement of the balloon catheter through a side arm graft. Subsequently, other techniques of IABP insertion were used. The most common technique involves placement of an insertion sheath/dialator into the femoral artery using standard Seldinger technique. This method avoids the necessity for having a vascular surgeon perform the IABP insertion procedure and, as a result, expanded the application of IABP therapy. Catheter insertion sets generally comprise a catheter and a catheter insertion sheath which is a tube or sleeve. The tube is typically made of a polymeric synthetic material and serves as a guide channel to insert the catheter into a punctured blood vessel through which the catheter is inserted into a blood vessel. This tube may have a means for expansion, usually by splitting as the catheter is inserted. The presence of the insertion tube results in a much larger cross-sectional area of the femoral artery being obstructed than when a balloon catheter alone is inserted. Consequently, after the catheter is inserted, it is preferable to remove the insertion tube. Further, the end of the tube, itself, can become the site for blood clotting and/or aggravation to the patient at the puncture site.

Although it is desirable to remove the insertion sheath, this is frequently not done. Some physicians are able to remove the insertion sheath after insertion of the catheter, but this removal is very sensitive to the skill and technique of the physician. Often, when removing the tube, the physician causes further trauma to the patient and additional bleeding. Consequently, as a rule, the puncture site is enlarged, provides opportunity for formation of blood vessel fissures at the puncture site, bleeding occurs and the potential for infection is increased.

A convenient method for preventing bleeding when a catheter insertion sheath is removed would permit more physicians to remove the insertion sheaths, thereby aiding blood flow.

SUMMARY OF THE INVENTION

We have found that bleeding around a catheter can be stopped when the insertion sheath is removed by providing the catheter with a tapered hemostatic device that can be moved along the catheter tube into the puncture site. The tapered hemostatic device of the present invention has an inner diameter that is just sufficient to permit the catheter tube to slide therethrough and a tapered outer diameter which at the distal end of the device is slightly larger than the inside diameter and at the proximal end of the device is at least as large as the outside diameter of the insertion sheath used to place the catheter in the blood vessel. The hemostatic device of the present invention is used to stop bleeding when the insertion sheath is removed from the blood vessel and the catheter. The hemostatic device is moved down the catheter into the puncture site where the taper stops the bleeding. Preferably, the hemostatic device stops the bleeding before the distal end enters the blood vessel. However, even if it is necessary to enter the blood vessel to stop bleeding the distal end of the hemostatic device is smaller than the insertion catheter and provides less obstruction to blood flow. Thereafter, a hemostasis cuff may be used at the proximal end of the device to stop blood flow between the tapered hemostatic device of the invention and the catheter In a preferred embodiment, the hemostatic device contains a longitudinal channel along the wall of the device. Preferably, this channel is along the inner wall of the device. This channel permits blood to flow therethrough when the distal end of the device enters the blood vessel thereby serving as an indicator to the physician or the health care professional that the hemostatic device is in the blood vessel

BRIEF DESCRIPTION OF DRAWINGS

FIG. 10a–b shows in elevation the device in use. FIG. 10a shows the device and cap on a catheter tube before insertion. FIG. 10b shows the device inserted into the puncture site. FIG. 10c shows the hemostasis cuff attached to the inserted device.

FIG. 11a shows in section an embodiment of the present invention having an alternate means for stopping blood flow between the tapered hemostatic device and the catheter. FIG. 11b shows the blood flow stopping means in use.

DESCRIPTION OF THE INVENTION

Figure 1:
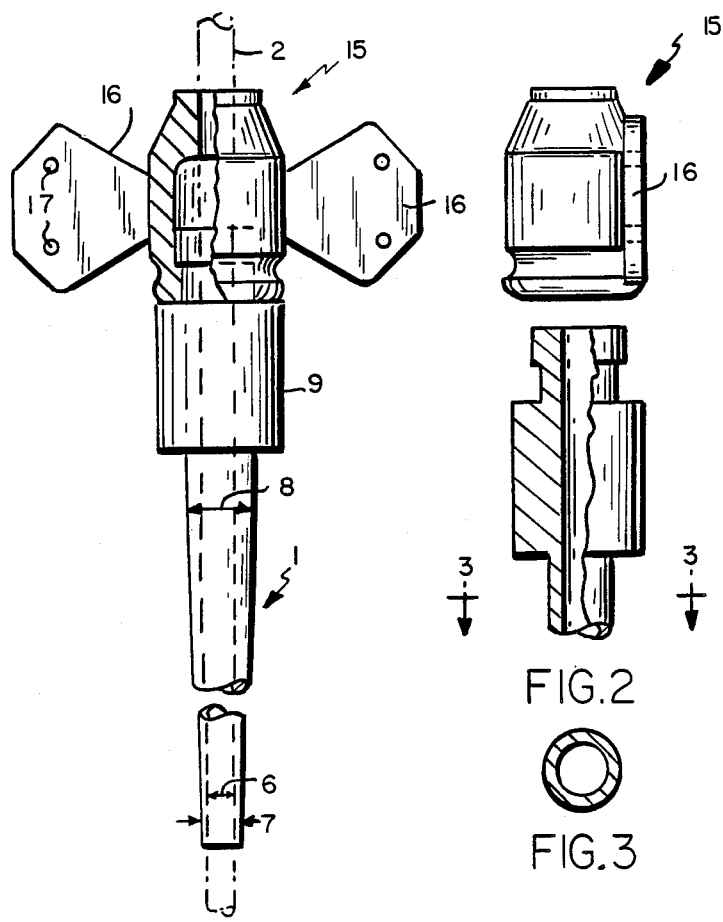
FIG. 1 is a side view of a hemostatic device and hemostasis cuff according to the present invention in cross section.
Figure 2:
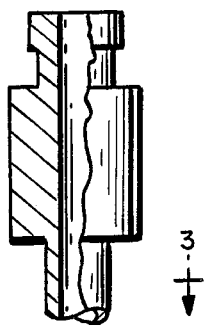
FIG. 2 is similar to FIG. 1 and shows the device from a different angle with the cuff removed
Figure 3:
FIG. 3 is a cross-section of the embodiment of FIG. 2.

We have now discovered a method for removal of an insertion sheath that can be readily practiced by most physicians. This technique comprises having a tapered device 1 on the catheter tube 2, wherein the inner diameter 6 of the device is just sufficient to slide over the catheter tube, and the outer diameter 7 at the distal end $d_1$ is just slightly larger than the inside diameter (See FIGS. 1 and 2), and tapers outwardly from the distal to the proximal end. The outer diameter 8, $d_2$, of the device at the proximal end is just slightly larger than the diameter of the insertion sheath. This sheath is relatively short in length, h, generally about 25 mm to about 75 mm preferably about 50 mm to about 75 mm, the exact length depending upon the depth of the flesh through which the catheter is inserted before entering the blood vessel. The length of the device is preferably long enough to enter the blood vessel for a short distance should that be required to stop bleeding. Preferably, there is also a separate hemostasis cuff 15 which is placed upon the device after it is in position (FIG. 1). Preferably, the cuff has wing tips 16 on either side which can be used to insure the device will not be moved by suturing through holes 17 or by taping the wings to the patient. This cuff can be secured to the device by a variety of methods well known in the art. Preferably the device has an enlarged section ("handle") 9 at the proximal end to facilitate handling. For example, the cuff can be screwed onto the handle (See FIG. 11), it can be popped into place (FIG. 1) or locked to the handle of the device by using a luer type of locking mechanism 18 (FIGS. 6–9). The cuff is placed over the luer type of lock and turned to lock into position 19. After the catheter is inserted into the patient, the insertion sheath is removed and the tapered device of this invention provides a means for stopping the flow of blood, resulting from the removal of the insertion catheter. See FIGS. 10 a-b. The device is advanced down the catheter tube (FIG. 10a). The distal end is advanced slowly into the puncture site until the bleeding stops (FIG. 10b). The device preferably stops the bleeding without entering the blood vessel 21 in which the catheter has been inserted. Consequently, the tapered device in accord with the invention stops the flow of blood that can result around the catheter after the insertion sheath is removed. Because of the size of the tapered device of the invention and its nature, even if it must be inserted into the blood vessel to stop bleeding it results in a smaller or at most no greater obstruction to blood flow than the insertion sheath. After the device has been positioned the hemostasis cuff is advanced down the catheter tube and secured onto the end of the device (FIG. 10c). The hemostasis cuff (e.g. 15 in FIG. 1 or 24 in FIG. 11a) can then be secured to the patient.

The tapered device of the present invention in preferred embodiment will also have a separate means 9 for the practicioner to move the device down the catheter tube. This means is at the proximal end of the device and preferably an integral part thereof as illustrated in FIG. 1. For example, in the embodiment shown in FIG. 1, the means is a handle 9 to provide sensitive control, although any of a number of configurations well known to those skilled in the art are possible.

Figure 4:
FIG. 4 is similar to FIG. 3 and shows another embodiment of the present invention where an indicator channel is included.
Figure 5:
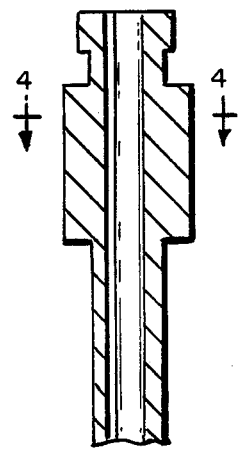
FIG. 5 shows in elevation the embodiment of FIG. 4 from the side.
Figure 6:
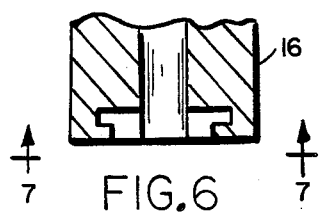
FIG. 6 shows in elevation a section of one embodiment of a hemostasis cuff used in accord with one embodiment of the present invention.
Figure 8:
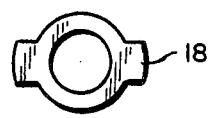
FIG. 8 shows a device according to the present invention from the top.
Figure 7:
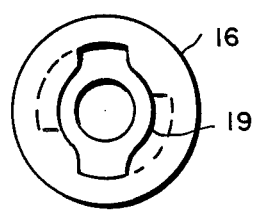
FIG. 7 shows the cuff of FIG. 6 in cross-section.
Figure 9:
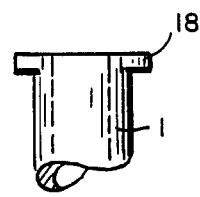
FIG. 9 is a side view of a portion of the device of FIG. 8.

In a preferred embodiment, the tapered device of this invention has an indicator channel 4 (FIGS. 4 and 5) preferably positioned axially along the inside wall of the device. This indicator channel permits the physician to determine when the device is in the blood vessel because blood flows through the channel which is sufficient to allow the flow of blood to indicate that the distal end is in the blood vessel. Generally, the channel is about both 1/64 of an inch wide and deep. Securing the hemostatis cuff on the device stops further blood flow.

In a preferred embodiment, the device contains a hemostasis cuff design as illustrated in FIGS. 11a and 11b. The inner diameter, $d_3$, within the proximal portion of the handle 9 of the device 25 is constructed so that is larger than the inner diameter, $d_4$, at the distal portion of the handle 26 immediately below. See FIG. 11a. This creates a shoulder within the handle. A cylindrical piece of elastomeric material 22 having an inner diameter when compressed that is less than the catheter tube and having an external diameter wider than $d_4$, and in its "relaxed" state having an external diameter that is less than $d_3$ and equal or slightly greater than $d_4$ is placed onto the catheter tubing. This elastomeric material will not be able to go lower than the shoulder within the handle. This elastomeric material may be placed into position in the device handle before the device is inserted because in its relaxed state blood from the indicator channel will be able to flow through the gap between the elastomeric cylinder and the catheter tube. In an alternative embodiment the elastomeric cylinder is slid into place within the device only after the device has been inserted into the puncture site to stop any blood flow that might occur. In either embodiment the elastomeric material is then compressed by using a cuff 24 that has an internal ring 27 which will compress the elastomeric material between the handle shoulder and the cuff ring as the cuff is tightened onto the device. See FIG. 11b. The elastomeric material when compressed 22' prevents the blood from the indicator channel from flowing through to the cuff. Preferably the handle and cuff in this embodiment are designed so that the cuff 24 can be screwed onto 23 the device handle. By controlling how the cuff is screwed on, the degree of compression of the elastomeric material can be controlled.

Any pharmacologically acceptable polymeric material can be used in preparing the catheter sheath. Such materials are well known in the field. Preferably, the tapered device is plastic. Even more preferably the device will be coated with a coagulent, especially at the distal end. Coagulents which can be used are well known to the person of ordinary skill in the art such as Avitene and the like. The device may also be coated with an antibiotic material to assist in keeping the wound clean. More preferably the device is coated with both an antibiotic and a coagulent. The person of ordinary skill in the art can determine appropriate antibiotics that can be used and which will not adversely affect or be affected by the coagulent by any of a number of well known source materials in the area, for example, the Physician's Desk Reference.

Additionally, when it is expected that the device might remain in place for a long time it can be made of a porous matrix material that will promote tissue ingrowth, for example, a collagen matrix, tetrafluoroethylene, polymeric fluorinated ethylene propylene.

In one embodiment, the device is constructed so that is has a slight curve at the distal end to assist the catheter in lying flat.

In a preferred embodiment, the tapered device is assembled with the catheter comprising a catheter set having a means for inserting the catheter, preferably an insertion sheath, all packaged in a pharmacologically acceptable container.

This invention has been described in detail with reference to the preferred embodiments thereof. However, it will be appreciated that those skilled in the art, upon consideration of this disclosure, may make modifications and improvements within the spirit and scope of the invention.

We claim:

1. A catheter set comprising (1) a balloon catheter having a catheter tube and (2) a hemostatic device, slidably mounted on the catheter tube; wherein the hemostatic device has an inner diameter just sufficient to permit the catheter tube to slide through, and has an outer diameter tapered from the distal end of the device to the proximal end of the device, which outer diameter is just larger than the inner diameter at the distal end of the device and, at the proximal end of the device, is predetermined to be at least as large as the external diameter of the means to be used to insert the catheter into the blood vessel of the patient.

2. The catheter set of claim 1, wherein the means for inserting the catheter is an insertion sheath.

3. The catheter set of claim 1 wherein the, wherein the length of the hemostatic device is about 75 mm to 25 mm.

4. The catheter set of claim 3 wherein the catheter sheath is about 50 mm to 25 mm.

5. The catheter set of claim 1, wherein the hemostatic device further comprises a channel positioned longitudinaly along the inner surface of the device to permit blood flow therethrough when the distal end is in a blood vessel.

6. The catheter set of claim 1 which further comprises a hemostasis cuff for the device that has an inner diameter just sufficient for the catheter tube to slide through.

7. The catheter set of claim 5 which further comprises a hemostasis cuff for the device that has an inner diameter just sufficient for the catheter tube to slide through and not sufficient for blood to flow through.

8. The catheter set of claim 5 wherein the set contains a means for stopping the blood flow through the indicator channel.

9. A method of removing a catheter insertion sheath from a catheter and catheter tube after a catheter has been inserted into the femoral artery comprising:
(a) removing the catheter insertion sheath;
(b) sliding a tapered hemostatic device down the catheter tube into the puncture site so that blood flow around the catheter is stopped; wherein the device has an inner diameter just sufficient to permit the catheter tube to go through and an outer diameter tapered from a distal end which is just larger than the inner diameter to a proximal end which is at least as large as the insertion sheath.

10. The method of claim 9 wherein the hemostatic device has a means for indicating when the device enters a blood vessel.

11. The method of claim 9 which further comprises a hemostasis cuff that has an inner diameter just sufficient for the catheter tube to slide through and not sufficient for blood to flow through which can be attached to the device to prevent blocking the blood flow from the indicator channel.

12. A hemostatic device comprising an inner diameter just sufficient to permit a catheter tube to slide through, and an outer diameter tapered from a distal end which is just larger than the inner diameter to a proximal end which is at least as large as the external diameter of a means used for inserting a catheter, and is coated with at least a coagulent or an antibiotic.

13. The hemostatic device of claim 12 where the device is coated with both a coagulent and an antibiotic.

14. The device of claim 12 where the device is composed of a porous matrix material.

15. A hemostatic device comprising an inner diameter just sufficient to permit a catheter tube to slide through, and an outer diameter tapered from a distal end which is just larger than the inner diameter to a proximal end which is at least as large as the external diameter of a means used for inserting a catheter, and a channel positioned lengthwise along the inner surface of the device to permit blood flow therethrough when the distal end is in a blood vessel.

16. The device of claim 15 wherein the device contains a means for stopping the blood flow through the indicator channel.

17. The device of claim 16 wherein the means for stopping blood flow is a cylindrical elastomeric material which is positioned at the proximal end of the device, wherein the device at the more proximial portion of the proximal end has an internal diameter, $d_3$, that is greater than the internal diameter immediately below, $d_4$, wherein the elastomeric material has an external diameter that when relaxed is wider than $d_4$ but narrower than $d_3$, and an internal diameter when compressed that is less than the catheter tube, and a means for placing a hemostasis cuff onto the device at its proximal end, where the cuff has a means for compressing the elastomeric material.

18. A catheter set comprising a catheter, and catheter tube, means for inserting the catheter into a blood vessel, and a hemostatic device, moveably mounted to the catheter tube; wherein the hemostatic device has an inner diameter just sufficient to permit the catheter tube to slide through, and an outer diameter tapered from the distal end which is just larger than the inner diameter to the proximal end which is at least as large as the external diameter of the means for inserting the catheter;
wherein the hemostatic device further comprises a channel positioned longitudinally along the inner surface of the device to permit blood flow therethrough when the distal end is in a blood vessel; and
wherein the set contains a means for stopping the blood flow through the indicator channel, which means for stopping blood flow comprises a cylindrical elastomeric material which is positioned at the proximal end of the device, wherein the device at the more proximal portion of the proximal end has an internal diameter, $d_3$, that is greater than the internal diameter, $d_4$, thus forming a shoulder;
wherein the elastomeric material has an external diameter that when relaxed is as wide or wider than $d_4$ but narrower than $d_3$ to abut the shoulder, and an internal diameter when compressed that is less than the catheter tube, and wherein a hemostasis cuff is placed onto the device at its proximal end, where the cuff has a means for compressing the elastomeric material to form a seal.

19. A hemostatic device comprising an inner diameter just sufficient to permit a catheter tube to slide through, and an outer diameter tapered from a distal end which is just larger than the inner diameter to a proximal end which is at least as large as the external diameter of a means used for inserting a catheter, and a channel positioned lengthwise along the inner surface of the device to permit blood flow therethrough when the distal end is in a blood vessel;
wherein the device contains a means for stopping the blood flow through the indicator channel, which, means for stopping blood flow comprises a cylindrical elastomeric material which is positioned at the proximal end of the device, wherein the device at the more proximal portion of the proximal end has an internal diameter, $d_3$, that is greater than the internal diameter, $d_4$, thus forming a shoulder;
wherein the elastomeric material has an external diameter that when relaxed is wider than $d_4$ but narrower than $d_3$ to abut the shoulder, and an internal diameter when compressed that is less than the catheter tube, and a means for placing a hemostasis cuff onto the device at its proximal end, where the cuff has a means for compressing the elastomeric material to form a seal.

* * * * *